United States Patent [19]

Rentzea et al.

[11] Patent Number: 4,515,616
[45] Date of Patent: May 7, 1985

[54] TRIAZOLYL KETONE-OXIMES AND TRIAZOLYL DIOXIMES, THEIR PREPARATION AND THEIR USE AS PLANT GROWTH REGULATORS

[75] Inventors: Costin Rentzea, Heidelberg; Wolfgang Spiegler, Ludwigshafen; Johann Jung, Limburgerhof, all of Fed. Rep. of Germany

[73] Assignee: BASF Aktiengesellschaft, Fed. Rep. of Germany

[21] Appl. No.: 498,757

[22] Filed: May 27, 1983

[30] Foreign Application Priority Data

May 28, 1982 [DE] Fed. Rep. of Germany ....... 3220183

[51] Int. Cl.³ .................. A01N 43/64; A01N 47/24; C07D 249/08; C07F 1/00
[52] U.S. Cl. .......................................... 71/76; 71/78; 71/92; 548/101; 548/262; 564/254; 564/255; 564/256; 564/258; 564/265; 564/268
[58] Field of Search .............. 548/101, 262; 71/76, 71/78, 92

[56] References Cited

U.S. PATENT DOCUMENTS

| | | | |
|---|---|---|---|
| 3,156,554 | 11/1964 | Tolbert | 71/2.7 |
| 4,360,526 | 11/1982 | Zeeh et al. | 424/269 |
| 4,385,354 | 5/1983 | Rentzea et al. | 71/76 |

FOREIGN PATENT DOCUMENTS

| | | | |
|---|---|---|---|
| 3005899 | 3/1981 | Fed. Rep. of Germany | 548/262 |
| 1593687 | 7/1981 | United Kingdom | 548/262 |

Primary Examiner—Alton D. Rollins
Attorney, Agent, or Firm—Keil & Weinkauf

[57] ABSTRACT

Triazolyl ketone-oximes and triazolyl dioximes of the general formula I

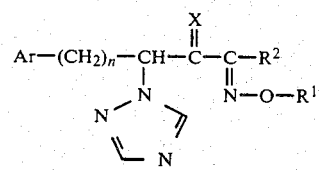

where
Ar is an aryl radical from the group comprising biphenylyl, naphthyl and phenyl, which radical can be substituted by halogen, nitro, cyano or trifluoromethyl, by alkyl, alkoxy or alkenyl, each of not more than 5 carbon atoms or by phenoxy, and n is 1 or 2,
X is oxygen or $=N-OR^3$, $R^3$ being hydrogen, unsubstituted, halogen-substituted or alkoxy-substituted alkyl, alkenyl or alkynyl, each of not more than 5 carbon atoms, or benzyl which is unsubstituted or substitutedby halogen, nitro, cyano or trifluoromethyl, or by alkyl or alkoxy, each of not more than 4 carbon atoms, or is $-CO-R^4$,
$R^4$ being unsubstituted, halogen-substituted or alkoxy-substituted alkyl of not more than 5 carbon atoms, an aromatic radical or $-NH-R^5$, $R^5$ being alkyl or not more than 4 carbon atoms or an aromatic radical,
$R^1$ is unsubstituted or alkoxy-substituted alkyl of not more than 8 carbon atoms or unsubstituted or substituted phenylalkyl, and
$R^2$ is alkyl of not more than 8 carbon atoms, their preparation and their use as growth regulators.

5 Claims, No Drawings

TRIAZOLYL KETONE-OXIMES AND TRIAZOLYL DIOXIMES, THEIR PREPARATION AND THEIR USE AS PLANT GROWTH REGULATORS

The present invention relates to novel triazolyl ketone-oximes and triazolyl dioximes, processes for their preparation, plant growth regulators containing these compounds and a method of regulating plant growth with these compounds.

It has been disclosed that certain 2-haloethyltrialkylammonium halides possess plant growth-regulating properties (cf. U.S. Pat. No. 3,156,554). For example, (2-chloroethyl)-trimethylammonium chloride can be used to influence plant growth. However, the activity of this compound is not always satisfactory, particularly when low amounts are used.

It has also been disclosed that 1-(4-bromophenyl)-1-allyloxy-2-(1,2,4-triazol-1-yl)-ethane can be used for regulating the growth of, in particular, rape, wheat, oats, rye and barley (German Laid-Open Application DOS No. 2,650,831). However, its action is not always satisfactory, particularly when low amounts are used.

We have found that compounds of the formula I

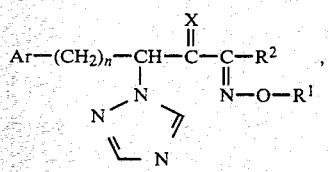

where

Ar is an aryl radical from the group comprising biphenylyl, naphthyl and phenyl, which radical can be substituted by halogen, nitro, cyano or trifluoromethyl, by alkyl, alkoxy or alkenyl, each of not more than 5 carbon atoms or by phenoxy, and n is 1 or 2, X is oxygen or $=N-OR^3$, $R^3$ being hydrogen, unsubstituted, halogen-substituted or alkoxy-substituted alkyl, alkenyl or alkynyl, each of not more than 5 carbon atoms, or benzyl which is unsubstituted or substituted by halogen, nitro, cyano or trifluoromethyl, or by alkyl or alkoxy, each of not more than 4 carbon atoms, or is $-CO-R^4$, $R^4$ being unsubstituted, halogen-substituted or alkoxy-substituted alkyl of not more than 5 carbon atoms, an aromatic radical or $-NH-R^5$, $R^5$ being alkyl of not more than 4 carbon atoms or an aromatic radical, $R^1$ is unsubstituted or alkoxy-substituted alkyl of not more than 8 carbon atoms or unsubstituted or substituted phenylalkyl, and $R^2$ is alkyl of not more than 8 carbon atoms, and their plant-tolerated salts and metal complexes, are very useful for influencing plant growth and are very well tolerated by plants.

The novel compounds of the formula I can occur in the Z or E steric forms, but mixtures are obtained in most cases. In the case of some of the novel compounds, the Z and E isomers can be separated by, for example, solubility differences or column chromatography, and can be isolated in pure form. The pure isomers are likewise embraced by the present invention. The pure Z and E geometric isomers as well as the mixtures of these obtained in the synthesis can be used as agents for influencing plant growth. For economic reasons, mixtures are preferably used, but in some cases sterically pure compounds have a more advantageous specific action.

Ar is, for example, biphenylyl, naphth-1-yl, naphth-2-yl, phenyl, 2- or 4-fluorophenyl, 3- or 4-chloro-phenyl, 4-bromophenyl, 4-methoxyphenyl, 4-ethoxyphenyl, 4-propoxyphenyl, 4-methylphenyl, 2,4-dimethylphenyl, 4-ethylphenyl, 4-propylphenyl, 4-n-butylphenyl, 4-isobutylphenyl, 4-tert.-butylphenyl, 4-pentylphenyl, 4-phenoxy-phenyl, 4-nitrophenyl, 3- or 4-trifluoromethylphenyl, 4-cyanophenyl, 4-allylphenyl, 3,4-dichlorophenyl, 2,4-dichlorophenyl or 2,6-dichlorophenyl, X is, for example, oxygen or $=N-O-R^3-$, $R^3$ is, for example, hydrogen, methyl, ethyl, 2-methoxyethyl, n-propyl, isopropyl, n-butyl, isobutyl, allyl, but-2-en-1-yl, pentenyl, propargyl, benzyl, 4-fluorobenzyl, 4-chlorobenzyl, 4-trifluoromethylbenzyl, 4-nitrobenzyl, 4-bromobenzyl, 4-methylbenzyl, 4-tert.-butylbenzyl, 2,4-dichlorobenzyl, 3,4-dichlorobenzyl or 2,6-dichlorobenzyl. $R^4$ is, for example, methyl, chloromethyl, bromomethyl, methoxymethyl, ethyl-2-chloroethyl, n-propyl, isopropyl or benzyl, $R^5$ is, for example, methyl, ethyl, propyl, n-butyl, phenyl or 4-chlorophenyl, $R^1$ is, for example, methyl, ethyl, 2-methoxyethyl, n-propyl, isopropyl, n-butyl, isobutyl, n-pentyl, isopentyl, n-hexyl, n-octyl, benzyl, 4-chlorobenzyl, 2,4-dichlorobenzyl, 4-bromobenzyl or 2-phenylethyl, and $R^2$ is, for example, methyl, ethyl, n-propyl, isopropyl, n-butyl, isobutyl, tert.-butyl, n-pentyl or n-heptyl.

Triazolyl ketone-oximes and triazolyl dioximes of the formula I are obtained if a ketone-oxime of the formula

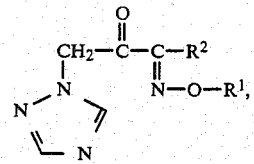

where $R^1$ and $R^2$ have the above meanings, or its alkali metal enolate, is reacted with an arylalkyl-halide of the formula $$Ar-(CH_2)_n-Y \qquad III,$$

where Ar and n have the above meanings and Y is chlorine, bromine or iodine, the resulting compound of the formula I, in which X is initially oxygen, is reacted with hydroxylamine, or with a salt thereof, to give an oxime of the formula I in which X is $=N-OH$, the dioxime thus obtained is reacted with an alkylating agent of the formula $$R^3-Y \qquad IV$$

or with an acid chloride of the formula $R^4-COCl$ or with an acid anhydride of the formula $(R^4-CO)_2O$ or with an isocyanate of the formula $R^5-N=C=O$ or with a carbamyl chloride of the formula $R^5-NH-COCl$, in which $R^3$, $R^4$ and $R^5$ have the above meanings and Y is chlorine, bromine or iodine, and, if desired, the resulting compound is converted with an acid to an addition salt, or with a metal salt to a metal complex. Under certain circumstances, the reactions may be carried out in a different sequence.

The reaction of a ketone-oxime (II) with an arylalkyl halide (III) is carried out in the presence or absence of a solvent or diluent, and preferably after the addition of a strong inorganic base, at an adequate temperature of, in general, below 120° C., preferably from 0° to 100° C. Preferred solvents include dimethylformamide, diethylformamide, dimethylacetamide, diethylacetamide, N-methylpyrrolidone, hexamethylphosphorotriamide, dimethylsulfoxide and sulfolane.

Examples of suitable bases or acid acceptors are alkali metal hydrides, such a lithium hydride, sodium hydride and potassium hydride, alkali metal amides, such as sodium amide, potassium amide, sodium diisopropylamide and potassium diisopropylamide, alkali metal alcoholates, such as sodium and potassium methoxide, ethoxide and tert.-butoxide, lithium-triphenylmethyl, sodium-triphenylmethyl, potassium-triphenylmethyl, naphthalene-lithium, naphthalene-sodium and naphthalene-potassium.

The ketone-oximes (II) are likewise novel. As is evident to one skilled in the art from a knowledge of their structural formula, these compounds can be obtained by reacting a known 1-halo-3-oximino-3-alkylpropan-2-one (V)

(V)

with 1,2,4-triazole. A suitable method of carrying out this reaction is given in the Preparation Examples.

The reaction of a compound of the formula I in which X is oxygen with hydroxylamine or a hydroxylamine salt is advantageously carried out in water or in a water-miscible solvent. These include, for example, alcohols, e.g. methanol, ethanol, propanol, ethylene glycol or 2-methoxyethanol, ethers, e.g. tetrahydrofuran or dioxane, acid amides, e.g. dimethylformamide, diethylformamide, dimethylacetamide, N-methylpyrrolidone or hexamethylphosphorotriamide, and acids, e.g. formic acid, acetic acid or propionic acid. Moreover, it is advantageous to add a base, eg. sodium hydroxide, potassium hyroxide, barium hydroxide or sodium acetate, an amine, e.g. triethylamine, piperidine or N-methylpiperidine, or an acid, eg. hydrochloric acid, sulfuric acid, phosphoric acid, formic acid or acetic acid.

The reaction is carried out in general at below 80° C., in most cases at from 0° to 40° C.

The reaction of the triazolyl dioxime of the formula I where X is N—OH with an alkylating agent, an acid chloride, an acid anhydride, an isocyanate or a carbamyl chloride can be carried out in the absence of a diluent or in a suitable solvent. These include, for example, acetonitrile, ethers, such as diethyl ether, dipropyl ether, dibutyl ether, methyl tert.-butyl ether, tetrahydrofuran, dioxane and dimethoxyethane, esters, such as ethyl acetate, ketones, such as acetone and methyl ethyl ketone, chlorohydrocarbons, such as methylene chloride, chloroform, carbon tetrachloride, dichloroethane, 1,1,1-trichloroethane, tetrachloroethane and chlorobenzene and hydrocarbons, such as benzene, toluene and xylene. Moreover, it is advantageous to add a base, for example an alkali metal hydroxide or alkaline earth metal hydroxide, such as sodium hydroxide, potassium hyroxide, calcium hydroxide or barium hydroxide, an alkali metal carbonate or alkaline earth metal carbonate, such as sodium carbonate, potassium carbonate, sodium bicarbonate, potassium bicarbonate, calcium carbonate or barium carbonate, an alkali metal alcoholate or alkaline earth metal alcoholate, such as sodium methylate, sodium ethylate, magnesium methylate, sodium isopropylate or potassium tert.-butylate, or an amine, such as triethylamine, N,N-dimethylcyclohexylamine, piperidine, N-methylpiperidine or pyridine.

Examples of suitable reaction accelerators are metal halides, such as sodium bromide, sodium iodide, potassium bromide potassium iodide, tertiary amines, such as 4-dimethylaminopyridine or 4-pyrrolidinopyridine, crown ethers, such as 12-crown-4, 14-crown-5, 18-crown-6, dibenzo-18-crown-6 or dicyclohexano-18-crown-6, and azoles, such as imidazole or 1,2,4-triazole.

Suitable phase-transfer catalysts are quaternary ammonium salts, e.g. tetrabutylammonium chloride, bromide, iodide or hydrogen sulfate, benzyltriethylammonium chloride or methyltrioctylammonium chloride or bromide, and phosphonium salts, e.g. tetrabutylphosphonium bromide or iodide or tetra-n-pentylphosphonium bromide or iodide.

The resulting compounds of the formula I are isolated by a conventional method, if appropriate purified and, if desired, reacted with an acid to give a salt, or with a metal salt to give a metal complex.

The Examples which follow illustrate the preparation of the novel compounds.

EXAMPLE 1

(a) Preparation of an intermediate (V)

A solution of 144 g (0.74 mole) of 1-bromo-3-methoximinobutan-2-one (T. Wieland and J. Stärke, Chem. Ber., 96, (1963), 2410) in 200 ml of tetrahydrofuran is added dropwise, in the course of 2 hours, at 25° C., to a suspension of 68.2 g (0.75 mole) of sodium 1,2,4-triazolide in 250 ml of dry tetrahydrofuran, the suspension being stirred under pure nitrogen. The mixture is stirred for a further 2 days at 25° C. and thereafter for 3 hours at 60° C. The resulting precipitate is filtered off, the filtrate is evaporated down under reduced pressure, the residue is dissolved in 300 ml of methylene chloride, and the solution is washed with three times 50 ml of water, dried over sodium sulfate and evaporated down under reduced pressure. The residue is stirred with 80 ml of ether and kept overnight at +3° C., and the precipitate is filtered off under suction, washed with 30 ml of cold (+5° C.) ether and thereafter with 100 ml of n-pentane, and is then dried.

56 g (41% of theory) of 1-(1,2,4-triazol-1-yl)-3-methoximinobutan-2-one are obtained as pale yellow crystals of melting point 87°–89° C.

(b) Preparation of the end product

A solution of 36.4 g (0.2 mole) of 1-(1,2,4-triazol-1-yl)-3-methoximinobutan-2-one in 50 ml of dimethylformamide is added dropwise, at from 20° to 25° C., to a suspension of 5 g (0.21 mole) of sodium hydride in 100 ml of dry dimethylformamide, the suspension being stirred under pure nitrogen. Stirring is continued for 3 hours, after which a solution of 32.2 g (0.2 mole) of 4-chlorobenzyl chloride in 35 ml of dimethylformamide is added dropwise at 25° C., and the mixture is stirred for a further 15 hours. 40 ml of ice water are carefully added dropwise, and the mixture is evaporated down under reduced pressure. The residue is partitioned between 300 ml of methylene chloride and 80 ml of water, and the organic phase is washed with three times 100 ml of water, dried over Na$_2$SO$_4$ and evaporated down. The residue is stirred with 30 ml of ether and kept at +3° C. for 3 hours, and the precipitate is filtered off under suction, washed with 10 ml of cold (+5° C.) ether and thereafter with 80 ml of petroleum ether, and is then dried.

35.6 g (58% of theory) of 1-(4-chlorophenyl)-2-(1,2,4-triazol-1-yl)-4-methoximinopentan-3-one are obtained as white crystals of melting point 87°–88° C.

EXAMPLE 2

18 g (0.1 mole) of a 30% strength solution of sodium methylate in methanol is added dropwise, at 20° C., to a solution of 7.6 g (0.11 mole) of hydroxylamine hydrochloride in 100 ml of ethanol. A solution of 20 g (0.07 mole) of the 1-(4-chlorophenyl)-2-(1,2,4-triazol-1-yl)-4-methoximinopentan-3-one obtained as described in Example 1, in 100 ml of ethanol, is then added, and the mixture is stirred for 3 days at 60° C. and then cooled to −5° C. The precipitate is filtered off under suction, washed in succession with 30 ml of ice water, 10 ml of cold (+5° C.) ethanol and 30 ml of ether, and then dried.

14.9 g (66.2% of theory) of 1-(4-chlorophenyl)-2-(1,2,4-triazol-1-yl)-3-hydroximino-4-methoximinopentane are obtained as colorless crystals of melting point 162°–164° C.

EXAMPLE 3

A mixture of 8 g (0.025 mole) of 1-(4-chlorophenyl)-2-(1,2,4-triazol-1-yl)-3-hydroximino-4-methoximinopentane, 0.5 g of imidazole and 50 ml of propionic anhydride is stirred for 12 hours at 60° C. and then evaporated down under reduced pressure. The residue is dissolved in 150 ml of ether, the solution is stirred for 30 minutes with 50 ml of a 6% strength sodium bicarbonate solution, and the organic phase is dried over sodium sulfate and evaporated down under reduced pressure, finally at not more than 70° C. and under 0.2 mbar.

8.2 g (86.8% of theory) of 1-(4-chlorophenyl)-2-(1,2,4-triazol-1-yl)-3-propionyloximino-4-methoximinopentane are obtained as a pale brown resin.

IR (film): 2980, 2950, 1773, 1489, 1362, 1345, 1272, 1135, 1048, 1012, 895, 815 and 680 cm$^{-1}$.

EXAMPLE 4

8.3 g (0.046 mole) of a 30% strength solution of sodium methylate in methanol are added dropwise, at 20° C., to a solution of 15.6 g (0.043 mole) of 1-(4-tert.-butylphenyl)-2-(1,2,4-triazol-1-yl)-3-hydroximino-4-methoximinopentane (cf. Example 78) in 100 ml of methanol. A solution of 7.9 g (0.046 mole) of benzyl bromide in 15 ml of tetrahydrofuran is then added, and the mixture is stirred for 15 hours at 20° C. and evaporated down under reduced pressure. The residue is partitioned between 200 ml of methylene chloride and 70 ml of water, and the organic phase is washed with three times 50 ml of water, dried over $Na_2SO_4$ and evaporated down. The residue is dissolved in 35 ml of petroleum ether, the solution is seeded and kept for 16 hours in a refrigerator, and the resulting white precipitate is filtered off under suction, washed with 10 ml of cold (−5° C.) petroleum ether and dried.

16 g (85.7% of theory) of 1-(4-tert.-butylphenyl)-2-(1,2,4-triazol-1-yl)-3-benzyloximino-4-methoximinopentane of melting point 108°–110° C. are obtained.

The compounds listed in the Table below can be obtained by appropriate modification of the above Preparation Examples.

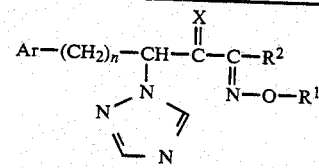

| No. | Ar | X | R$^1$ | R$^2$ | n | Physical constant or infrared spectrum [cm$^{-1}$] (film) |
|---|---|---|---|---|---|---|
| 5 | 4-BrC$_6$H$_4$— | O | —CH$_3$ | —CH$_3$ | 1 | m.p. 107–109° C. |
| 6 | " | =N—OH | " | " | 1 | m.p. 170–172° C. |
| 7 | " | CH$_3$—NH—CO—O—N= | " | " | 1 | resin |
| 8 | C$_6$H$_5$— | O | " | " | 1 | m.p. 70–72° C. |
| 9 | " | =N—OH | " | " | 1 | m.p. 140–142° C. |
| 10 | " | O | n-C$_3$H$_7$ | " | 1 | 3030, 2965, 2878 1695, 1595, 1490 1268, 1200, 1130 1020, 750, 700 |
| 11 | " | O | " | " | 2 | 3028, 2964, 2880 1695, 1595, 1492 1358, 1270, 1130 1055, 1020, 750 |
| 12 | " | =N—OH | " | " | 1 | m.p. 123–124° C. |
| 13 | 1-C$_{10}$H$_7$ | O | —CH$_3$ | " | 1 | m.p. 138–140° C. |
| 14 | " | =N—OH | " | " | 1 | m.p. 198–200° C. |
| 15 | " | 4-FC$_6$H$_4$—CH$_2$—O—N= | " | " | 1 | 3060, 2940, 1605 1511, 1276, 1224 1047, 1021, 1014 902, 825, 799, 781 |
| 16 | " | 2,6-Cl$_2$C$_6$H$_3$—CH$_2$—O—N= | " | " | 1 | m.p. 122–132° C. |
| 17 | 4-FC$_6$H$_4$ | O | " | " | 1 | m.p. 93–95° C. |
| 18 | " | =N—OH | " | " | 1 | m.p. 141–143° C. |
| 19 | " | CH$_2$=CH—CH$_2$—O—N= | " | " | 1 | 2940, 2822, 1605 1511, 1276, 1224 1139, 1053, 1023 985, 903, 679 |

-continued

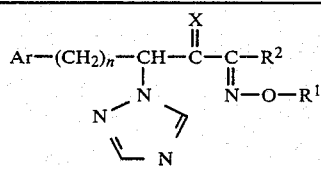

| No. | Ar | X | R¹ | R² | n | Physical constant or infrared spectrum [cm⁻¹] (film) |
|---|---|---|---|---|---|---|
| 20 | 3-ClC₆H₄— | O | " | " | 1 | 2976, 2940, 1695 1590, 1492, 1268 1130, 1045, 888 782, 690, 678 |
| 21 | " | =N—OH | " | " | 1 | m.p. 136–138° C. |
| 22 | 4-ClC₆H₄— | O | —C₂H₅ | " | 1 | resin |
| 23 | " | =N—OH | " | " | 1 | m.p. 161–162° C. |
| 24 | " | 4-ClC₆H₄—CH₂—O—N= | " | " | 1 | 2982, 2940, 1494 1367, 1276, 1208 1139, 1092, 1048 1015, 956, 890 801 |
| 25 | 4-ClC₆H₄ | 4-BrC₆H₄—CH₂—O—N= | " | " | 1 | resin |
| 26 | " | 4-(CF₃)C₆H₄—CH₂—O—N= | " | " | 1 | resin |
| 27 | " | n-C₄H₉—O—N= | " | " | 1 | resin |
| 28 | " | CH₃—O—CH₂CH₂—O—N= | " | " | 1 | resin |
| 29 | " | O | —C₃H₇—n | " | 1 | 2968, 2935, 1695 1590, 1484, 1268 1200, 1055, 1035 815, 678 |
| 30 | " | =N—OH | " | " | 1 | m.p. 141–143° C. |
| 31 | " | CH₃—C(=O)—O—N= | " | " | 1 | resin |
| 32 | " | Cl—CH₂—C(=O)—O—N= | " | " | 1 | resin |
| 33 | " | O | —C₄H₉—n | " | 1 | 2970, 2880, 1698 1603, 1495, 1370 1278, 1140, 1035 880, 820, 678 |
| 34 | " | =N—OH | " | " | 1 | m.p. 142–146° C. |
| 35 | " | CH₃—CH₂—C(=O)—O—N= | " | " | 1 | resin |
| 36 | 4-ClC₆H₄— | O | C₆H₅—CH₂— | " | 1 | 3025, 2925, 1695 1590, 1480, 1355 1266, 1130, 1005 870, 812, 734 695 |
| 37 | " | =N—OH | " | " | 1 | m.p. 184–186° C. (isomer I) |
| 38 | " | =N—OH | " | " | 1 | m.p. 146–148° C. (isomer-mixture) |
| 39 | " | O | —CH₃ | —C₂H₅ | 1 | m.p. 78–80° C. |
| 40 | " | =N—OH | " | " | 1 | m.p. 171–174° C. |
| 41 | " | CH₃—CH₂—C(=O)—O—N= | " | " | 1 | resin |
| 42 | 3,4-Cl₂C₆H₃ | O | " | —CH₃ | 1 | m.p. 106–108° C. |
| 43 | " | =N—OH | " | " | 1 | m.p. 169–171° C. |
| 44 | 2,4-Cl₂C₆H₃— | O | " | " | 1 | m.p. 107–109° C. |
| 45 | " | =N—OH | " | " | 1 | m.p. 220–222° C. (isomer E) |
| 46 | " | =N—OH | " | " | 1 | m.p. 158–160° C. (isomer Z) |
| 47 | 2,4-Cl₂C₆H₃ | CH₃—CH₂—C(=O)—O—N= | " | " | 1 | 2975, 2940, 1774 1580, 1496, 1466 1360, 1278, 1130 1100, 1045, 876 |

-continued

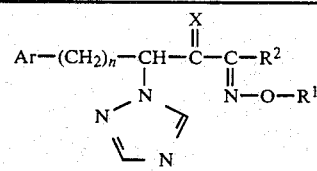

| No. | Ar | X | R¹ | R² | n | Physical constant or infrared spectrum [cm$^{-1}$] (film) |
|---|---|---|---|---|---|---|
| 48 | " | $C_6H_5-\overset{O}{\underset{\|}{C}}-O-N=$ | " | " | 1 | resin |
| 49 | " | O | $-C_2H_5$ | " | 1 | m.p. 83–85° C. |
| 50 | " | $=N-OH$ | " | " | 1 | m.p. 127–128° C. |
| 51 | " | $CH_3-CH_2-\overset{O}{\underset{\|}{C}}-O-N=$ | " | " | 1 | resin |
| 52 | " | O | n-$C_3H_7$ | " | 1 | 2960, 1692, 1580 1490, 1465, 1268 1035, 920, 862 825, 676 |
| 53 | " | $=N-OH$ | " | " | 1 | m.p. 131–134° C. |
| 54 | " | $CH_3-CH_2-\overset{O}{\underset{\|}{C}}-O-N=$ | " | " | 1 | resin |
| 55 | " | O | $-CH_3$ | n-$C_4H_9$ | 1 | 2960, 2937, 1707 1592, 1502, 1475 1276, 1138, 1104 1046, 678 |
| 56 | " | $=N-OH$ | " | " | 1 | m.p. 137–139° C. |
| 57 | 2,4-$Cl_2C_6H_3-$ | $Cl-CH_2CH_2-\overset{O}{\underset{\|}{C}}-O-N=$ | " | " | 1 | resin |
| 58 | " | $CH_3CH_2-\overset{O}{\underset{\|}{C}}-O-N=$ | " | " | 1 | resin |
| 59 | " | O | " | i-$C_4H_9$ | 1 | 2961, 2938, 1707 1593, 1502, 1475 1390, 1276, 1137 1103, 1047, 835 |
| 60 | " | $=N-OH$ | " | " | 1 | m.p. 160–162° C. |
| 61 | " | $CH_3-CH=CH-CH_2-O-N=$ | " | " | 1 | resin |
| 62 | " | $CH_3CH_2-\overset{O}{\underset{\|}{C}}-O-N=$ | " | " | 1 | resin |
| 63 | 4-$(CH_3)C_6H_4-$ | O | " | $-CH_3$ | 1 | m.p. 84–86° C. |
| 64 | " | $=N-OH$ | " | " | 1 | m.p. 166–168° C. |
| 65 | " | $CH_3-CH_2-\overset{O}{\underset{\|}{C}}-O-N=$ | " | " | 1 | 2970, 2932, 1775 1495, 1456, 1345 1270, 1135, 1108 1045, 880, 805 |
| 66 | " | O | $-C_2H_5$ | " | 1 | resin |
| 67 | " | $=N-OH$ | " | " | 1 | m.p. 138–140° C. (Isom. I) |
| 68 | " | $=N-OH$ | " | " | 1 | m.p. 177–178° C. (isomer mixture) |
| 69 | " | O | $-C_3H_7-n$ | " | 1 | 2970, 2940, 1708 1505, 1440, 1368 1278, 1138, 1060 1035, 810, 678 |
| 70 | " | $=N-OH$ | " | " | 1 | m.p. 198–200° C. (isomer I) |
| 71 | " | $=N-OH$ | " | " | 1 | m.p. 117–120° C. (isomer mixture) |
| 72 | " | O | $-C_6H_{13}-n$ | " | 1 | resin |
| 73 | " | $=N-OH$ | " | " | 1 | resin |
| 74 | 4-$(C_2H_5)C_6H_4-$ | O | $-CH_3$ | " | 1 | 2965, 2938, 1695 |

-continued

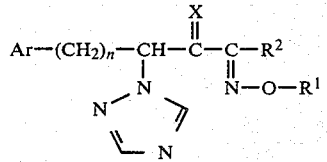

| No. | Ar | X | R¹ | R² | n | Physical constant or infrared spectrum [cm⁻¹] (film) |
|-----|-----|-----|-----|-----|-----|-----|
|  |  |  |  |  |  | 1596, 1495, 1430 |
|  |  |  |  |  |  | 1270, 1132, 1045 |
|  |  |  |  |  |  | 822, 760, 678 |
| 75 | " | =N—OH | " | " | 1 | m.p. 118–120° C. |
| 76 | " | 4-(CH₃)C₆H₄—CH₂—O—N= | " | " | 1 | 2964, 2935, 1516 |
|  |  |  |  |  |  | 1502, 1445, 1366 |
|  |  |  |  |  |  | 1275, 1695, 1592 |
|  |  |  |  |  |  | 1016, 898, 810 |
| 77 | 4-(tert.-C₄H₉)C₆H₄— | O | " | " | 1 | 2955, 1695, 1592 |
|  |  |  |  |  |  | 1492, 1355, 1266 |
|  |  |  |  |  |  | 1128, 1040, 949 |
|  |  |  |  |  |  | 873, 818, 675 |
| 78 | " | =N—OH | " | " | 1 | m.p. 144–150° C. |
| 79 | 4-(NO₂)C₆H₄— | O | " | " | 1 | m.p. 204–206° C. (isomer E) |
| 80 | " | O | " | " | 1 | m.p. 103–105° C. (isomer Z) |
| 81 | " | =N—OH | " | " | 1 | m.p. 172–174° C. |
| 82 | 4-(CN)C₆H₄— | O | " | " | 1 | resin |
| 83 | " | =N—OH | " | " | 1 | resin |
| 84 | 2,4-(CH₃)₂C₆H₃— | O | " | " | 1 | m.p. 68–71° C. |
| 85 | " | =N—OH | " | " | 1 | m.p. 113–115° C. |
| 86 | " | 4-(tert.-C₄H₉)C₆H₄—CH₂—O—N= | " | " | 1 | 2963, 1502, 1465 |
|  |  |  |  |  |  | 1445, 1364, 1275 |
|  |  |  |  |  |  | 1140, 1052, 1015 |
|  |  |  |  |  |  | 969, 889, 676 |
| 87 | 4-(CF₃)C₆H₄— | O | " | " | 1 | 2948, 1707, 1620 |
|  |  |  |  |  |  | 1503, 1325, 1277 |
|  |  |  |  |  |  | 1166, 1124, 1068 |
|  |  |  |  |  |  | 1049, 1..9, 822 |
|  |  |  |  |  |  | 677 |
| 88 | " | =N—OH | " | " | 1 | m.p. 162–166° C. |
| 89 | " | CH₃CH₂C(=O)—O—N= | " | " | 1 | 2988, 2945, 1782 |
|  |  |  |  |  |  | 1503, 1326, 1277 |
|  |  |  |  |  |  | 1165, 1126, 1069 |
|  |  |  |  |  |  | 1053, 1019, 895 |
| 90 | " | C₂H₅—O—N= | " | " | 1 |  |
| 91 | " | O | —C₂H₅ | " | 1 |  |
| 92 | " | =N—OH | " | " | 1 |  |
| 93 | " | CH₃CH₂C(=O)—O—N= | " | " | 1 |  |

The new active ingredients may have different influences on virtually all development stages of a plant, and are therefore used as plant growth regulators.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased suspectibility to freeze injury and—because of the relatively low leaf or plant mass—attack by various diseases, especially fungus diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of trees.

The action of the novel compounds is superior to that of prior art growth regulators. This action is manifested not only in monocotyledon crops, e.g., cereals such as wheat, barley, rye, oats and rice or Indian corn or grasses, but also particularly in dicotyledons (e.g., sunflowers, tomatoes, groundnuts, grapes, cotton, rape and, particularly, soybeans) and various ornamentals such as chrysanthemums, poinsettias and hibiscus.

The compounds according to the invention may be applied to the crop either by treating the seed, treating the soil, i.e., through the roots, or—the method particularly preferred—by spraying the leaves.

Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.1 to 12 kg/ha, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine, ketones, e.g. cyclohexanone, dimethylformamide, and water; solid carriers, for example natural rock powders, e.g. kaolin, alumina, talc and chalk, and synthetic rock powders, e.g. highly disperse silica and silicates; emulsifiers, and other surfactants, for example non-ionic and anionic emulsifiers, e.g. polyoxyethylene fatty alcohol ethers and alkylsulfonates, and dispersants, for example lignin, sulfite waste liquors and methylcellulose. It is preferred to use the compounds according to the invention in aqueous solution, if desired with the addition of water-miscible organic solvents such as methanol or other lower alcohols, acetone, dimethylformamide or N-methylpyrrolidone. The formulations in general contain from 0.1 to 95% by weight of active ingredient, preferably from 0.5 to 90%.

The formulations, and the ready-to-use preparations obtained therefrom, e.g. solutions, emulsions, suspensions, powders, dusts, pastes or granules, are applied in the conventional manner, e.g., preemergence, post-emergence, or as seed disinfectants.

Examples of formulations are given below:

I. 20 parts by weight of the compound of Example 2 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight the of compound of Example 3 is intimately mixed with 97 parts by weight of particulate kaolin. A dust is obtained containing 3% by weight of the active ingredient.

III. 30 parts by weight of the compound of Example 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 47 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04% wt% of active ingredient.

V. 20 parts of the compound of Example 52 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 16 is mixed with 10 parts by weight of N-methyl-alpha-pyrrolidone. A mixture is obtained which is suitable for application in the form of very fine drops.

VII. 20 parts by weight of the compound of Example 88 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 89 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IX. 20 parts by weight of the compound of Example 87 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

The agents according to the invention many, in these application forms, also be mixed and applied with other active ingredients, e.g., herbicides, insecticides, other growth regulators, fungicides and fertilizers. When mixed with other growth regulators, the spectrum of action is in many cases increased; with a number of these compositions, synergistic effects also occur; i.e., the action of the combination product is greater than the effect of the individual components added together.

Examples of fungicides which may be combined with the compounds according to the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis-(thiocarbamoyl)-disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitrophenol derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimido-phosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenyl-hydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, D,L-methyl-N-(2,6-dimethylphenyl)-N-fur-2-yl-alanate, methyl D,L-N-(2,6-dimethylphenyl)-N-(2'-methoxyacetyl)-alanate, diisopropyl 5-nitroisophthalate, 2,5-dimethyl-furan-3-carboxylic acid anilide, 2,5-dimethylfuran-3-carboxylic acid cyclohexylamide, 2-methyl-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, 2,3-dichloro-1,4-naphthoquinone, 1,4-dichloro-2,5-dimethoxybenzene, p-dimethylaminobenzene diazine sodium sulfonate, 1-chloro-2-nitropropane, polychloronitrobenzenes, such as pentachloronitrobenzene, methyl isocyanate, fungicidal antibiotics, such as grisofulvin and kasugamycin, tetrafluorodichloroacetone, 1-phenylthiosemicarbazide, Bordeaux mixture, nickel-containing compounds, and sulfur.

To determine the growth-regulating properties of the candidate compounds, soil provided with sufficient nutrients was filled into plastic pots about 12.5 cm in diameter and test plants were growth therein.

For the preemergence treatment, the candidate compounds were poured, as aqueous formulations, onto the seedbed on the day of sowing.

For the postemergence treatment, the compounds were sprayed onto the plants. The growth-regulating action observed was confirmed at the end of the experiment by height measurements. The values obtained were compared with those for untreated plants.

The compounds used for comparison purposes were chlorocholine chloride (A) and a triazolyl ketone (B), disclosed in German Laid-Open Application DOS No. 2,739,352, Example 2:

A (CCC)

$$CH_3-\overset{\underset{\displaystyle CH_3}{|}}{\underset{\underset{\displaystyle CH_3}{|}}{N^{\oplus}}}-CH_2-CH_2-Cl\ Cl^{\ominus}$$

B (German Laid-Open Application DOS 2,739,352 Example 2)

[Structure: 4-chlorophenyl-C(=O)-CH₂-CH(t-Bu)-N(1,2,4-triazole)]

Not only was growth height reduced—the leaves also took on a more intense color. The increased chlorophyll content is indicative of a higher rate of photosynthesis, making for bigger yields.

| Spring barley, "Union" variety; preemergence | | |
|---|---|---|
| Ex. no. | mg/vessel | Relative growth height |
| — | — | 100 |
| A (comparative compound) | 3 | 86.0 |
| | 12 | 78.0 |
| 12 | 3 | 85.5 |
| | 12 | 59.5 |
| 88 | 3 | 56.6 |
| | 12 | 49.1 |

| Lawn; postemergence | | |
|---|---|---|
| Ex. no. | mg/vessel | Relative growth height |
| — | — | 100 |
| A (comparative compound) | 1.5 | 88.5 |
| | 6.0 | 88.5 |
| 12 | 1.5 | 96.8 |
| | 6.0 | 80.6 |
| 88 | 1.5 | 74.3 |
| | 6.0 | 58.6 |

| Sunflowers; "Sobrid" variety; postemergence | | |
|---|---|---|
| Ex. no. | mg/vessel | Relative growth height |
| — | — | 100 |
| A (comparative compound) | 1.5 | 89.5 |
| | 6.0 | 84.4 |
| B (comparative compound) | 1.5 | 98.9 |
| | 6.0 | 95.3 |
| 3 | 1.5 | 88.1 |
| | 6.0 | 82.7 |
| 63 | 1.5 | 90.6 |
| | 6.0 | 75.5 |
| 69 | 1.5 | 84.5 |
| | 6.0 | 84.5 |
| 70 | 1.5 | 89.5 |
| | 6.0 | 84.5 |
| 75 | 1.5 | 92.1 |
| | 6.0 | 74.2 |
| 87 | 1.5 | 86.6 |
| | 6.0 | 70.9 |
| 88 | 1.5 | 84.6 |
| | 6.0 | 73.1 |

| Spring rape, "Petranova" variety; preemergence | | |
|---|---|---|
| Ex. no. | mg/vessel | Relative growth height |
| — | — | 100 |
| A (comparative compound) | 3 | 95.1 |
| | 12 | 90.2 |
| B (comparative compound) | 3 | 95.1 |
| | 12 | 78.1 |

-continued

| Spring rape, "Petranova" variety; preemergence | | |
|---|---|---|
| Ex. no. | mg/vessel | Relative growth height |
| 2 | 3 | 23.7 |
| | 12 | 15.8 |
| 3 | 3 | 31.5 |
| | 12 | 15.8 |
| 6 | 3 | 35.5 |
| | 12 | 23.7 |
| 9 | 3 | 74.8 |
| | 12 | 58.4 |
| 18 | 3 | 35.5 |
| | 12 | 11.9 |
| 19 | 3 | 75.6 |
| | 12 | 48.8 |
| 23 | 3 | 72.0 |
| | 12 | 38.1 |
| 39 | 3 | 86.9 |
| | 12 | 70.5 |
| 40 | 3 | 61.1 |
| | 12 | 43.7 |
| 43 | 3 | 51.2 |
| | 12 | 39.4 |
| 46 | 3 | 74.8 |
| | 12 | 55.2 |
| 47 | 3 | 67.0 |
| | 12 | 47.3 |
| 50 | 3 | 84.7 |
| | 12 | 63.6 |
| 64 | 3 | 35.5 |
| | 12 | 21.7 |
| 65 | 3 | 82.5 |
| | 12 | 51.5 |
| 67 | 3 | 67.8 |
| | 12 | 50.8 |
| 68 | 3 | 82.6 |
| | 12 | 72.0 |
| 75 | 3 | 77.1 |
| | 12 | 56.1 |
| 81 | 3 | 51.2 |
| | 12 | 31.5 |
| 84 | 3 | 91.1 |
| | 12 | 67.8 |
| 85 | 3 | 89.0 |
| | 12 | 67.8 |
| 87 | 3 | 87.8 |
| | 12 | 73.2 |
| 88 | 3 | 13.6 |
| | 12 | 13.6 |

| Spring rape, "Petranova" variety; postemergence | | |
|---|---|---|
| Ex. no. | mg/vessel | Relative growth height |
| — | — | 100 |
| A (comparative compound) | 1.5 | 91.3 |
| | 6.0 | 84.5 |
| B (comparative compound) | 1.5 | 99.1 |
| | 6.0 | 94.8 |
| 2 | 1.5 | 73.4 |
| | 6.0 | 68.8 |
| 3 | 1.5 | 57.3 |
| | 6.0 | 48.5 |
| 18 | 1.5 | 77.1 |
| | 6.0 | 63.9 |
| 18 | 1.5 | 61.7 |
| | 6.0 | 55.1 |
| 36 | 1.5 | 90.1 |
| | 6.0 | 77.3 |
| 39 | 1.5 | 77.0 |
| | 6.0 | 64.1 |
| 40 | 1.5 | 72.4 |
| | 6.0 | 67.9 |
| 43 | 1.5 | 55.1 |
| | 6.0 | 48.5 |
| 46 | 1.5 | 59.5 |
| | 6.0 | 48.5 |
| 47 | 1.5 | 55.1 |
| | 6.0 | 50.7 |
| 50 | 1.5 | 73.0 |
| | 6.0 | 60.1 |

-continued

| Spring rape, "Petranova" variety; postemergence | | |
|---|---|---|
| Ex. no. | mg/vessel | Relative growth height |
| 55 | 1.5 | 81.2 |
|  | 6.0 | 66.3 |
| 56 | 1.5 | 63.3 |
|  | 6.0 | 58.8 |
| 59 | 1.5 | 83.4 |
|  | 6.0 | 64.1 |
| 64 | 1.5 | 66.1 |
|  | 6.0 | 55.1 |
| 75 | 1.5 | 72.3 |
|  | 6.0 | 68.2 |
| 76 | 1.5 | 77.3 |
|  | 6.0 | 60.4 |
| 81 | 1.5 | 52.9 |
|  | 6.0 | 48.5 |
| 87 | 1.5 | 82.2 |
|  | 6.0 | 73.1 |
| 88 | 1.5 | 70.0 |
|  | 6.0 | 62.8 |

We claim:

1. Triazolyl ketone-oximes and triazolyl dioximes of the formula

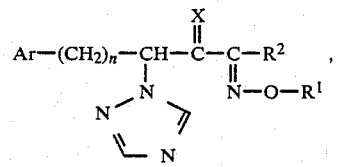

where Ar is an aryl radical from the group consisting of biphenylyl, naphthyl and phenyl, which radical can be substituted by halogen, nitro, cyano or trifluoromethyl, by alkyl, alkoxy or alkenyl, each of not more than 5 carbon atoms, or by phenoxy, and n is 1 or 2, X is oxygen or $=N-OR^3$, $R^3$ being hydrogen, unsubstituted, halogen-substituted or alkoxy-substituted alkyl, alkenyl or alkynyl, each of not more than 5 carbon atoms, or benzyl which is unsubstituted or substituted by halogen, nitro, cyano or trifluoromethyl, or by alkyl or alkoxy, each of not more than 4 carbon atoms, or is $-CO-R^4$, $R^4$ being unsubstituted, halogen-substituted or alkoxy-substituted alkyl of not more than 5 carbon atoms, phenyl, benzyl or $-NH-R^5$, $R^5$ being alkyl of not more than 4 carbon atoms, $R^1$ is unsubstituted or alkoxy-substituted alkyl of not more than 8 carbon atoms or benzyl, chloro-benzyl, bromo-benzyl or phenylethyl, and $R^2$ is alkyl of not more than 8 carbon atoms or plant tolerated salts and metal complexes thereof.

2. Triazolyl ketone-oximes and triazolyl dioximes of the formula I as defined in claim 1, where Ar is a radical selected from the group consisting of biphenylyl, naphth-1-yl, naphth-2-yl, phenyl, 2- and 4-fluorophenyl, 3- and 4-chlorophenyl, 4-bromophenyl, 4-methoxyphenyl, 4-ethoxyphenyl, 4-propoxyphenyl, 4-methylphenyl, 2,4-dimethylphenyl, 4-ethylphenyl, 4-propylphenyl, 4-n-butylphenyl, 4-isobutylphenyl, 4-tert.-butylphenyl, 4-pentylphenyl, 4-phenoxyphenyl, 4-nitrophenyl, 3- and 4-trifluoromethylphenyl, 4-cyanophenyl, 4-allylphenyl, 3,4-dichlorophenyl, 2,4-dichlorophenyl and 2,6-dichlorophenyl, n is 1 or 2, X is oxygen or $=N-O-R^3-$, $R^3$ being hydrogen or a radical selected from the group consisting of methyl, ethyl, 2-methoxyethyl, n-propyl, isopropyl, n-butyl, isobutyl, allyl, but-2-en-1-yl, pentenyl, propargyl, benzyl, 4-fluorobenzyl, 4-chlorobenzyl, 4-trifluoromethylbenzyl, 4-nitrobenzyl, 4-bromobenzyl, 4-methylbenzyl, 4-tert.-butylbenzyl, 2,4-dichlorobenzyl, 3,4-dichlorobenzyl, 2,6-dichlorobenzyl, or $CO-R^4$, $R^4$ being methyl, chloromethyl, bromomethyl, methoxymethyl, ethyl, 2-chloroethyl, n-propyl, isopropyl, benzyl, or $-NH-R^5$, $R^5$ being methyl, ethyl, propyl, n-butyl, phenyl or 4-chlorophenyl, $R^1$ is methyl, ethyl, 2-methoxyethyl, n-propyl, isopropyl, n-butyl, isobutyl, n-pentyl, isopentyl, n-hexyl, n-octyl, benzyl, 4-chlorobenzyl, 2,4-dichlorobenzyl, 4-bromobenzyl or 2-phenylethyl, and $R^2$ is methyl, ethyl, n-propyl, isopropyl, n-butyl, isobutyl, tert.-butyl, n-pentyl or n-heptyl.

3. Triazolyl ketone oximes of the formula

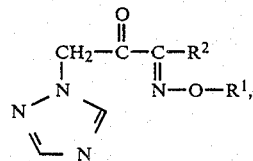

where $R^1$ and $R^2$ have the meanings given in claim 1.

4. A process for regulating plant growth which comprises allowing an effective amount of one or more compounds of the formula I of claim 1 to act on plants or their habitat.

5. A composition for regulating plant growth which comprises a solid or liquid carrier and an effective amount of at least one compound of the formula I of claim 1.

* * * * *

UNITED STATES PATENT AND TRADEMARK OFFICE
CERTIFICATE OF CORRECTION

PATENT NO. : 4,515,616

DATED : May 7, 1985

INVENTOR(S) : Costin RENTZEA et al.

It is certified that error appears in the above-identified patent and that said Letters Patent is hereby corrected as shown below:

IN THE ABSTRACT:

Line 15, delete "substitutedby" and insert --substituted by--.

Line 21, after "alkyl" insert --of-- and delete "or".

Signed and Sealed this

Seventeenth Day of September 1985

[SEAL]

Attest:

Attesting Officer

DONALD J. QUIGG

Commissioner of Patents and Trademarks—Designate